US011807660B2

(12) United States Patent
Angell et al.

(10) Patent No.: US 11,807,660 B2
(45) Date of Patent: Nov. 7, 2023

(54) PEPTIDE COMPOUND AND APPLICATION THEREOF, AND COMPOSITION CONTAINING PEPTIDE COMPOUND

(71) Applicant: XDCEXPLORER (SHANGHAI) CO., LTD., Shanghai (CN)

(72) Inventors: Yvonne Angell, Shanghai (CN); Yu Wu, Shanghai (CN); Yan Wang, Shanghai (CN); Weimin Liu, Shanghai (CN); Kin Chiu Fong, Shanghai (CN); Jie Wen, Shanghai (CN); Yonghan Hu, Shanghai (CN)

(73) Assignee: XDCEXPLORER (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 17/700,860

(22) Filed: Mar. 22, 2022

(65) Prior Publication Data

US 2022/0213142 A1    Jul. 7, 2022

Related U.S. Application Data

(62) Division of application No. 16/628,586, filed as application No. PCT/CN2018/094618 on Jul. 5, 2018, now Pat. No. 11,427,615.

(30) Foreign Application Priority Data

Jul. 5, 2017  (CN) .......................... 201710543383.0
Jul. 4, 2018  (CN) .......................... 201810725881.1

(51) Int. Cl.
C07K 7/06     (2006.01)
A61K 47/60    (2017.01)
A61P 35/04    (2006.01)
A61K 38/00    (2006.01)

(52) U.S. Cl.
CPC ................ C07K 7/06 (2013.01); A61K 47/60 (2017.08); A61P 35/04 (2018.01); *A61K 38/00* (2013.01)

(58) Field of Classification Search
CPC . C07K 7/06; C07K 7/08; C07K 14/47; A61K 47/60; A61K 38/00; A61P 35/04; A61P 15/00; A61P 15/08; A61P 25/24; A61P 35/00; A61P 5/00
See application file for complete search history.

(56) References Cited

U.S. PATENT DOCUMENTS

| 6,800,611 | B2 | 10/2004 | Fujii et al. |
| 7,625,869 | B2 | 12/2009 | Kitada et al. |
| 7,754,220 | B2 | 7/2010 | Ohtaki et al. |
| 7,960,348 | B2 | 6/2011 | Asami .................... A61P 15/08 514/19.8 |
| 8,361,986 | B2 | 1/2013 | Kandimalla et al. |
| 8,592,379 | B2 | 11/2013 | Fujii et al. |
| 8,765,909 | B2 | 7/2014 | Asami et al. |
| 8,878,871 | B2 | 11/2014 | Clark et al. |
| 2004/0180407 | A1 | 9/2004 | Watanabe et al. |
| 2005/0240008 | A1 | 10/2005 | Ohtaki et al. |
| 2009/0093615 | A1 | 4/2009 | Asami et al. |
| 2011/0171160 | A1 | 7/2011 | Minamitani ........... A61K 47/60 424/78.17 |
| 2015/0361138 | A1 | 12/2015 | Beltramo ................ C07K 7/00 514/19.3 |

FOREIGN PATENT DOCUMENTS

| CN | 101341168 A | 1/2009 | |
| CN | 101341168 B | 1/2013 | |
| CN | 106544322 A | 3/2017 | |
| JP | 2003002841 A | 1/2003 | |
| TW | 201906856 A | 12/2019 | |
| WO | 0024890 A1 | 5/2000 | |
| WO | 0175104 A1 | 10/2001 | |
| WO | 02085399 A1 | 10/2002 | |
| WO | 2007072997 A1 | 6/2007 | |
| WO | WO-2009131191 A1 | 10/2009 | ............. A61P 15/00 |
| WO | 2010033224 A1 | 3/2010 | |
| WO | WO-2014118318 A1 | 8/2014 | ............... C07K 7/00 |

OTHER PUBLICATIONS

Matsui et al (Endocrinology, 2012, 153(11), 5297-5308) (Year: 2012).*
Patani et al (Chem.Rev., 1996, 96, 3147-3176) (Year: 1996).*
Borics et al (Journal of Medicinal Chemistry, 2012, 55, 8418-8428) (Year: 2012).*
Schlesinger et al (New J. Chem., 2003, 27, 60-67) (Year: 2003).*
Malesevic et al (International Journal of Peptide Research and Therapeutics, vol. 2, No. 2, Jun. 2006, 165-177) (Year: 2006).*
Notice of Rejection dated Nov. 29, 2021 issued in corresponding Taiwan Application No. 107123335, with English translation, 14 pages.
First Office Action dated Jun. 15, 2021 issued in Taiwan Application No. 107123335, with English translation, 9 pages.
International Search Report dated Sep. 27, 2018 issued in International Patent Application No. PCT/CN2018/094618 with English translation, 9 pages.
Written Opinion of the International Searching Authority dated Sep. 27, 2018 issued in International Patent Application No. PCT/CN2018/094618 with English translation, 10 pages.
Partial Supplementary European Search Report dated Jul. 17, 2020 issued in corresponding EP Application No. 18828694.2, 13 pages.
Jiang, Fusheng, et al., "Research progress of polyethylene glycol prodrugs," Chin Pharm J, vol. 42, Issue 12, 2007, 13 pages.
Lee, Jeong-Hyung, et al., "KiSS-1, a novel human malignant melanoma metastasis-suppressor gene," Journal of the National Cancer Institute, vol. 88, No. 23, 1996, pp. 1731-1737.

(Continued)

*Primary Examiner* — Sudhakar Katakam
(74) *Attorney, Agent, or Firm* — SZDC Law PC

(57) ABSTRACT

Disclosed are a peptide compound and an application thereof, and a composition containing the peptide compound. The present invention provides a peptide compound represented by compound 3, and a pharmaceutically acceptable salt, a tautomer, a solvate, a crystal form or a prodrug thereof. The compound has good stability and good activity for Kiss1R.

Ac-(D-Tyr)-A6c-Asn-Thr-Phe-azaGly-Leu-Arg(Me)-Trp-$NH_2$

8 Claims, No Drawings

(56) References Cited

OTHER PUBLICATIONS

Ohtaki, T., et al., "Metastasis suppressor gene KiSS-1 encodes peptide ligand of a G-protein-coupled receptor," Letters to Nature, vol. 411, Issue 6837, 2001, pp. 613-617.

Kotani, Masato, et al., "The Metastasis Suppressor Gene KiSS-1 Encodes Kisspeptins, the Natural Ligands of the Orphan G Protein-coupled Receptor GPR54," J. Biol. Chem., vol. 276, 2001, pp. 34631-34636.

Nash, Kevin T., et al., "The KISS 1 metastasis suppressor: mechanistic insights and clinical utility," Frontiers in Bioscience, vol. 11, 2006, pp. 647-659.

Lee, Jeong-Hyung, et al., "Identification of highly expressed genes in metastasis-suppressed chromosome 6/human malignant melanoma hybrid cells using subtractive hybridization and differential display," Int. J Cancer, vol. 71, Issue 6, 1997, pp. 1035-1044.

Roa, J., et al., "Hypothalamic expression of KiSS-1 system and gonadotropin-releasing effects of kisspeptin in different reproductive states of the female Rat," Endocrinology, vol. 147, Issue 6, 2006, pp. 2864-2878.

Stahl, P. Heinrich, et al., "Handbook of Pharmaceutical Salts for a review of pharmaceutically acceptable salts: Properties, Selection, and Use," Chapter 4, Wiley-VCH, 2002, 34 pages.

Rautio, J., "Prodrugs: design and clinical applications," Nature Reviews | Drug Discovery, vol. 7, Issue 3, 2008, pp. 255-270.

Stella, Valentino J., et al., "Prodrugs: Challenges and rewards," Springer, 2007.

Lu, Gui-shen, et al., "Improved Synthesis of 4-Alkoxybenzyl Alcohol Resin," J. Org. Chem, vol. 46, Issue 17, 1981, pp. 3433-3436.

Asami, Taiji, et al., "Design, Synthesis, and Biological Evaluation of Novel Investigational Nonapeptide KISS1R Agonists with Testosterone-Suppressive Activity," Journal of Medicinal Chemistry, vol. 56, Issue 21, 2013, pp. 8298-8307.

Decourt, C., et al., "A synthetic kisspeptin analog that triggers ovulation and advances puberty," Scientific Reports, vol. 6, Issue 1, 2016, pp. 1-10.

Beltramo, Massimiliano, et al., Rational Design of Triazololipopeptides Analogs of Kisspeptin Inducing a Long-Lasting Increase of Gonadotropins, Journal of Medicinal Chemistry, vol. 58, Issue 8, 2015, pp. 3459-3470.

Asami, Taiji, et al., "Serum stability of selected decapeptide agonists of KISS1R using pseudopeptides," Bioorganic & Medicinal Chemistry Letters, vol. 22, Issue 20, 2012, pp. 6391-6396.

Extended European Search Report dated Dec. 10, 2020 issued in EP Application No. 18828694.2, 12 pages.

* cited by examiner

PEPTIDE COMPOUND AND APPLICATION THEREOF, AND COMPOSITION CONTAINING PEPTIDE COMPOUND

This application is a Divisional Application of U.S. patent application Ser. No. 16/628,586 filed on Jan. 3, 2020. U.S. Ser. No. 16/628,586 is a U.S. National Phase Application under 35 U.S.C. 371 of International Application No. PCT/CN2018/094618 filed on Jul. 5, 2018. This application claims the priority of Chinese patent application CN201710543383.0 filed on Jul. 5, 2017 and Chinese patent application CN201810725881.1 filed on Jul. 4, 2018. The content of said Chinese patent application is hereby incorporated by reference in its entirety.

FIELD OF INVENTION

The disclosure relates to a peptide compound and an application thereof, and a composition containing the peptide compound.

PRIOR ARTS

Kiss-1 gene is a novel type of gene that inhibit the metastasis of human melanoma discovered by Jeong-Hyung Lee et al. (Lee J H, et al. Journal of the national cancer institute, vol. 88 (23): 1731-1737 (1996)). Kiss-1 gene is located on human chromosome 1q32 and consists of four exons, two untranslated and two partially translated exons, which encodes a precursor polypeptide containing 145 amino acids. The precursor peptide is cleaved into 54 amino acid length Kisspeptin-54 (also known as metastin or transfer inhibitor), and can be further truncated to 14 [kisspeptin-14/metastin (40-54)], 13 [kisspeptin-13/metastin (41-54)], or 10 [kisspeptin-10/metastin (45-54)] amino acids. These truncations and precursors are collectively referred to as Kisspeptin (Kp) and are highly conserved in mammals (Kotanim, et. al. Journal of biological chemistry, vol. 276 (27): 34631-34636; Ohtaki T. et al., Nature Vol, 411(6837): 613-671 (2001)). The four kisspeptins all contain the same 10 amino acid residues, the C-terminal of which has arginine and amidated phenylalanine (RF-amide), but the N-terminal polypeptides differ in length. The C-terminal part of the kisspeptins is related to the efficient binding and activation of the receptors, and the activity of truncated peptides, for example Kisspeptin-10 and Kisspeptin-14 is 3-10 times higher than that of Kisspeptin-54. mRNA of the Kiss-1 is mainly expressed in human placenta and is also widely expressed in the whole central nervous system: the highest expression is in the shell, the higher expression is in caudate nucleus, globus pallidus, hypothalamus, nucleus accumbens and cerebellum, and the lower expression is in superior frontal gyms, amygdala, cingulate gyms, hippocampus, para hippocampal gyms, thalamus, substantia nigra, locus coeruleus and medulla oblongata, and the very low expression is in spinal cord.

At present, it is known that the receptor for these kisspeptins (Kiss1R) is a member of retinoic acid-inducible orphan G protein-coupled receptor family (namely GPR54 in rats and AXOR12 in humans). Kiss1R contains 398 amino acid residues and is related to the galanin receptor family, but it does not bind to galanin. Rat GPR54 is highly conserved in mammals and has 81% homology with human receptors and 85% homology with mice. The mRNA of human Kiss1R is expressed abundantly in placenta, pituitary, spinal cord and pancreas, and is expressed at a low level in other tissues including different parts of brain (thalamus, caudate nucleus, substantia nigra, hippocampus, amygdala, and cerebellum), stomach, small intestine, thymus, spleen, lung, testis, kidney and fetal liver. Kisspeptin and its receptors are distributed in brain and in various peripheral tissues and organs, including hypothalamus, aorta, ovary, prostate and placenta, and the receptors are also expressed in pituitary gland. Their functions include regulating reproductive function, affecting endocrine, and affecting the growth and metastasis of tumor cells.

The signal transmission between kisspeptin and Kiss1R (GPR54) is to activate phospholipase C(PLC) in the cell after the polypeptide binds with its receptor, and then hydrolyze phosphatidylinositol diphosphate (PIP2) to produce inositol triphosphate (IP3) and diacylglyceride (DAG), which promote the increasement of intracellular calcium ion, the realsing of arachidonic acid, the activation of protein kinase C(PKC), and the phosphorylation of the extracellular signal regulatory kinases (ERK1 and ERK2) and p38 mitotic activated protein kinase (MAPK), thus producing the biological effects. An important role of the signalling between Kisspeptin and Kiss1R is to start secreting gonadotropin-releasing hormone (GnRH) during puberty. The release of gonadotropin-releasing hormone is the behavior of the anterior pituitary gland, which also includes the release of luteinizing hormone, LH) and follicle stimulating hormone, FSH). Disruption of this signaling pathway will lead to insufficient GnRH release, resulting in hypogonadism in humans and rodents. Abnormal release or absence is the main cause of abnormal sexual reproduction for men and women. Studies have proved that GnRH analogue kisspeptin plays a role at hypothalamic level to stimulate GnRH release (U.S. Pat. No. 7,754,220). The input of kisspeptin can stimulate GnRH to release at all stages. The use of Kiss1R agonist is a method for preventing or treating hormone-related diseases for example prostate cancer, breast cancer, endometriosis, hysteromyoma, breast cancer before amenorrhea, central precocious puberty, sexual functional diseases, etc. It is also used in in vitro fertilization to induce ovulation and as a new generation of contraceptives.

The binding of the kisspeptin and Kiss1R (GPR54) has many functions, among which the inhibition of cell proliferation is an important one (Kotanim, et al., *J. Biol. Chem.* vol. 276: 34631-34636). Kiss1R agonist can inhibit cell proliferative diseases selected from the following disease groups: benign prostatic hyperplasia, prostate cancer, breast cancer, ovarian cancer, uterine cancer, cervical cancer, endometrial cancer, melanoma, pancreatic cancer, gastric cancer, renal cell cancer, esophageal cancer, bladder cancer, brain cancer, etc.

Kiss1 gene is initially named as Kiss1 metastasis inhibitory gene, which can manage tumor cell metastasis and has clinical value. The expression level of primary melanoma cell line expressing Kiss1 gene is negatively related to the metastatic potential of melanoma cell line. C8161 cells expressed Kiss1 gene, and lung metastasis was inhibited by more than 95% (Nash et al., The KISS1 metastasis suppressor: mechanistic insights and clinical utility, *Front. Biosci.* vol. 11, pp. 647-659 (2006)). Kisspeptin can reduce cell mobility and inhibit tumor cell metastasis by inducing excessive cell adhesion phenotype (Lee J H and Welch D R, *Int. J. Cancer,* vol. 71 (6): 1035-1044 (1997)). Metastin derivatives also have excellent biological activities (e.g., cancer cell metastasis inhibitory activity, cancer cell growth inhibitory activity, etc.) (U.S. 68061B2, U.S. Pat. Nos. 7,625,869B2, 8,361,986B2, 8,592,379B2). Kiss1R agonist inhibits tumor metastasis and migration, and affects the invasion of trophoblast cells, wherein said disease or disease state is selected from melanoma, pancreatic cancer, breast cancer, ovarian cancer, uterine cancer, cervical cancer, endometrial cancer, thyroid cancer, bladder cancer, esophageal squamous cell cancer, gastric cancer, liver cancer and other cancers.

Kiss1R (GPR54) is also highly expressed in the central nervous system (CNS) and the hippocampus region. It has been proved that, Kiss1R can reversibly enhance the synaptic transmission in hippocampal dentate gyrus cells through mechanisms involving MAP kinases, which appears to be regulated by calcium-activated kinases and tyrosine kinases (Roa J, Hypothalamic expression of KiSS-1 system and gonadotropin-releasing effects of kisspeptin in different reproductive states of the female Rat. et. al. Endocrinology 147(6): 1624-1632, 2006). Studies have proved that injection of kisspeptin can enhance limbic brain activity and produce sexual stimulation. Therefore, kisspeptin can stimulate sexual desire in essence and is related to the feeling of sex appeal, romance and sexual excitement. Kiss1R agonist can enhance the erotic signals from brain and emotion, thus treating sexual dysfunction caused by psychological reasons.

Kisspeptin also has the function of affecting placental function, therefore, Kiss1R agonist is effective in treating the disease or disease state selected from: choriocarcinoma, invasive nevus, abortion, fetal hypoplasia, abnormal glucose metabolism, abnormal lipid metabolism, etc. (WO00/24890; WO01/75104 2; WO 02/85399).

Takeda company has disclosed kisspeptin analog TAK448 in patents CN101341168B, U.S. Pat. Nos. 8,592,379B2, 8,765,909B2 and 9,778,871B2:

thereof, solvates thereof, crystal forms thereof or prodrugs thereof, wherein the peptide compound 3 has any of the following structures:

| Compound number | | Sequence |
|---|---|---|
| YA-172 | M10[Ac, D-Y45, A6c46, des47, T49, azaGly51, R(Me)53, W54] | Ac-(D-Tyr)-A6c-Asn-Thr-Phe-azaGly-Leu-Arg(Me)-Trp-NH$_2$ |
| YA-182 | M10[Ac, D-Phe(2,4-diCl)45, S-Pip46, des47, T49, azaGly51, R(Me)53, W54] | Ac[D-Phe(2,4-DiCl)]-(S-Pip)-Asn-Thr-Phe-azaGly-Leu-Arg(Me)-Trp-NH$_2$ |
| YA-255 | M10[Ac, D-Phe(2,4-diCl)45, Pro(diF)46, des47, T49, Gψ(NHCS)51, R(Me)53, W54] | Ac-D-Phe(2,4-DiCl)-DiFluorPro-Asn-Thr-Phe-ψ(NHCS)G-Leu-Arg(Me)-Trp-NH$_2$ |

The present disclosure also provides a use of the compound 3, the pharmaceutically acceptable salts, tautomers, crystal forms, solvates or prodrugs thereof in manufacturing a medicament for treating and/or preventing diseases related to kisspeptin receptors.

Said diseases related to kisspeptin receptor are, for example, hormone-related diseases, cell proliferative diseases, or diseases related to placental function.

Said hormone-related diseases are, for example, prostate cancer, breast cancer (e.g., breast cancer before amenorrhea), endometriosis, hysteromyoma, central precocious

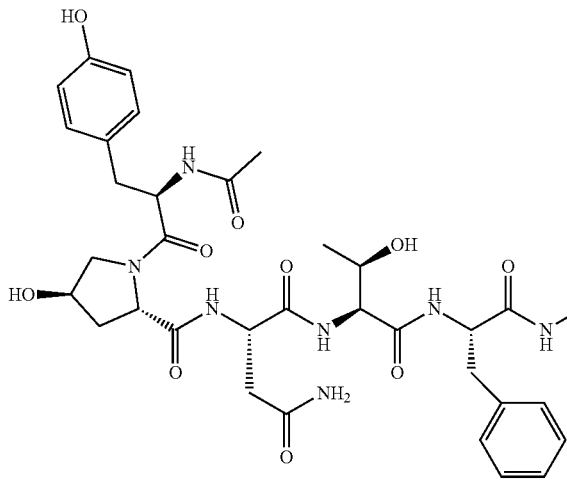
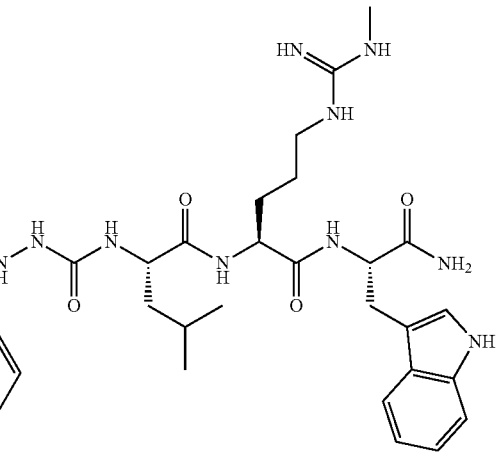

TAK448

Contents of the Present Disclosure

The technical problem to be solved by the present disclosure is that the existing peptide compound has low stability and low activity to Kiss1R. Therefore, the present disclosure provides a peptide compound, an application thereof and a composition containing the peptide compound, which has better stability and activity to Kiss1R.

The present disclosure also provides a peptide compound 3, pharmaceutically acceptable salts thereof, tautomers puberty, estrogen receptor positive, sexual functional diseases (e.g., sexual dysfunction, sexual apathy), infertility, depression, or pregnancy.

Said cell proliferative disease is, for example, benign prostatic hyperplasia or cancer. Said cancers as prostate cancer, breast cancer, ovarian cancer, uterine cancer, cervical cancer, endometrial cancer, thyroid cancer, bladder cancer, liver cancer, melanoma, pancreatic cancer, gastric cancer, renal cell cancer, esophageal cancer (such as esophageal squamous cell cancer), bladder cancer or brain cancer.

Said diseases related to placental function are, for example, choriocarcinoma, invasive nevus, abortion, fetal hypoplasia, abnormal glucose metabolism or abnormal lipid metabolism.

The present disclosure also provides a pharmaceutical composition comprising the compound 3, the pharmaceutically acceptable salts thereof, the tautomers thereof, the crystal forms thereof, the solvates thereof or the prodrugs thereof, and one or more pharmaceutical excipients.

The pharmaceutical excipients can be those widely used in the field of pharmaceutical production. Said excipients are mainly used to provide a safe, stable and functional pharmaceutical composition, and can also provide methods to enable the active ingredient to dissolve out at a desired rate after the subject receives administration, or to promote the effective absorption of the active ingredient after the subject receives administration of the composition. Said pharmaceutical excipients can be inert fillers or provide certain functions, such as stabilizing the overall pH value of the composition or preventing degradation of the active ingredients of the composition. The pharmaceutical excipients may include one or more of the following adjuvants: binder, suspending agents, emulsifier, diluent, filler, granulating agent, adhesive, disintegrating agent, lubricant, anti-adhesion agent, glidant, wetting agent, gelling agent, absorption delaying agent, dissolution inhibitor, reinforcing agent, adsorbent, buffer, chelating agent, preservative, colorant, flavoring agent and sweetener.

The pharmaceutical composition of the present disclosure can be prepared according to the disclosure using any method known to those skilled in the art, for example, conventional mixing, dissolving, granulating, emulsifying, grinding, encapsulating, embedding or lyophilizing processes.

The pharmaceutical composition of the present disclosure can be formulated for administration in any form, including injection (intravenous), mucosal, oral (solid and liquid preparations), inhalation, ocular, rectal, local or parenteral (infusion, injection, implantation, subcutaneous, intravenous, intra-arterial, intramuscular) administration. The pharmaceutical composition of the present disclosure may also be a controlled release or delayed release dosage form (e.g., liposome or microsphere). Examples of solid oral preparations include, but are not limited to, powders, capsules, caplets, soft capsules and tablets. Examples of liquid preparations for oral or mucosal administration include, but are not limited to, suspensions, emulsions, elixirs and solutions. Examples of topical preparations include, but are not limited to, emulsions, gels, ointments, creams, patches, pastes, foams, lotions, drops or serum preparations. Examples of preparations for parenteral administration include, but are not limited to, injectable solutions, dry preparations that can be dissolved or suspended in pharmaceutically acceptable carriers, injectable suspensions, and injectable emulsions. Examples of other suitable preparations of the pharmaceutical composition include, but are not limited to, eye drops and other ophthalmic preparations; aerosol: such as nasal spray or inhalant; liquid dosage forms suitable for parenteral administration; suppositories and lozenges.

On the basis of not violating common knowledge in the art, the above-mentioned preferred conditions can be combined arbitrarily to give various preferred examples of the present invention.

The reagents and raw materials used in the present disclosure are commercially available.

Unless otherwise specified, the terms used in the present invention have the following meanings:

The peptide molecules of the present invention are defined herein using conventional single letter codes for representing amino acids. The term "amino acid" includes water-soluble organic compounds having carboxyl (—COOH) and amino (—NH$_2$) groups attached to α-carbon atoms. The amino acid can be represented by the general formula R—CH(NH$_2$)COOH; said R group is a hydrogen or an organic group and determines the properties of any specific amino acid. Tetrahedral arrangement of four different groups around α-carbon atoms makes amino acids optically active. The two mirror image isomers are called L-isomer and D-isomer. Generally, only L-amino acids are components of proteins such as eukaryotic proteins.

Unless otherwise stated, the peptide molecules of the present disclosure comprise L-amino acids. When D-amino acid is present in the peptide molecule of the present disclosure, it is represented by a conventional single-letter amino acid code prefixed with "(D)".

As described, the molecule of the present disclosure may comprise or consist of a peptide sequence having "any D-amino acid" at a specific position. Said "any D-amino acid" includes any natural or unnatural (e.g., chemically modified) D-amino acid at a specific position in the sequence. Examples of natural D-amino acids are as follows: D-alanine; D-aspartic acid D-cysteine; D-glutamic acid; D-phenylalanine; D-glycine; D-histidine; D-isoleucine; D-lysine; D-leucine; D-methionine; D-asparagine; D-proline; D-glutamine; D-arginine; D-serine; D-threonine; D-valine; D-tryptophan; D-tyrosine. Examples of unnatural D-amino acids are as follows: naphthylalanine; D-pyridylalanine; D-tert-butylserine; D-ornithine; D-£ aminolysine; D-hyperarginine; D-α methylleucine and the substitution of halogens (e.g., F) for protons in these and other unnatural amino acids.

By forming peptide bonds, amino acids are combined to form short chains (peptides) or longer chains (polypeptides). It is known that proteins and/or peptides are composed of about 20 common amino acids with different mobile phase ratios, and their sequences determine the shape, properties and biological effects of proteins and/or peptides. Amino acid residues in the chain of such peptides or polypeptides are usually represented by their arrangement positions on the chain, and the first site (i.e., site 1) is designated as the amino acid at the N-terminus of the chain.

TABLE 1

| Explanation of Amino Acid Abbreviations | |
|---|---|
| Abbreviation | Full name |
| Ala | Alanine |
| Cys | Cysteine |
| Asp | Aspartic acid |
| Glu | glutamate |
| Phe | Phenylalanine |
| Gly | glycine |

TABLE 1-continued

Explanation of Amino Acid Abbreviations

| Abbreviation | Full name |
| --- | --- |
| His | histidine |
| Ile | Isoleucine |
| Lys | Lysine |
| Leu | leucine |
| Met | met |
| Asn | asparagine |
| Pro | proline |
| Gln | Glutamine |
| Arg | Arginine |
| Ser | Serine |
| Thr | Threonine |
| Val | val |
| Trp | Tryptophan |
| Tyr | tyr |
| D-Ala | D-alanine |
| D-Cys | D-cysteine |
| D-Asp | D-aspartic acid |
| D-Glu | D-glutamic acid |
| D-Phe | D-Phenylalanine |
| D-Gly | D-glycine |
| D-His | D-histidine |
| D-Ile | D-isoleucine |
| D-Lys | D-lysine |
| D-Leu | D-leucine |
| D-Met | D-methionine |
| D-Asn | D-asparagine |
| D-Pro | D-proline |
| D-Gln | D-glutamine |
| D-Arg | D-arginine |
| D-Ser | D-serine |
| D-Thr | D-threonine |
| D-Val | D-valine |
| D-Trp | D-tryptophan |
| D-Tyr, DTyr | D-tyrosine |
| Ac | Acetyl |
| cyc | The amino group of the N-terminal amino acid and the carboxyl group of the C-terminal amino acid are condensed to form an amide bond to form a ring. |
| Hyp | Trans-4-hydroxyproline |
| azaGly, azaG | Azoglycine |
| Arg(Me), R(Me) | N omega-methyl arginine, 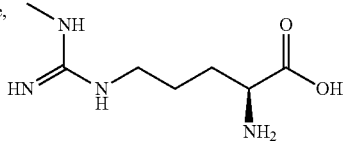 |
| N-Me-Arg, N-MeArg, NMeArg, NMe-Arg | N alpha-methyl arginine, 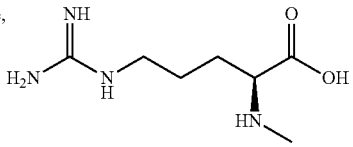 |
| αMePhe, α-Me-Phe, αMe-Phe, α-MePhe | Alpha-methyl phenylalanine, 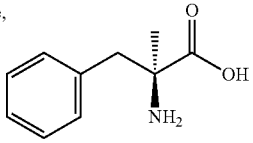 |
| NMePhe, N-Me-Phe, N-MePhe, NMe-Phe | N-methyl phenylalanine |
| N-Me-D-Phe, NMe-D-Phe | N-methyl-D-phenylalanine |

TABLE 1-continued

Explanation of Amino Acid Abbreviations

| Abbreviation | Full name |
|---|---|
| 1Nal, Nal1, Nal-1, 1-Nal | 1-naphthylalanine, |
| 2Nal, Nal2, Nal-2, 2-Nal | 2-naphthylalanine, |
| 4Pal, 4-Pal | 4-pyridylalanine, |
| Phe(4-F) | 4-fluorophenylalanine |
| αMeTyr, αMe-Tyr | Alpha-methyl tyrosine, |
| ψ(CH2NH)51 | The —CONH— bond between the 51st amino acid and the 52nd amino acid is replaced by the —CH$_2$NH— bond. |
| Ava | Delta-amyl acid, |
| Aib | Alpha-methyl alanine, |
| Sar | N-methylglycine, sarcosine |
| Chg | L-α-alpha-cyclohexylglycine, |
| Dap(Dnp) | N'-(2,4-dinitrophenyl)-L-2,3-diaminopropionic acid, |

TABLE 1-continued

Explanation of Amino Acid Abbreviations

| Abbreviation | Full name |
|---|---|
| D-Phe(2,4-diCl), D-Phe(2,4-DiCl) | 2,4-dichloro-D-phenylalanine |
| D-2Fua, 3-(2-furyl)-D-Ala, 3-(2-furyl)-D-Alanine | 3-(2-furyl)-D-alanine, |
| Pro(5Ph), Pro(5-phenyl) | (2S,5R)-5-phenylpyrrolidine-2-carboxylic acid |
| Thz | 4-thioproline |
| Phe(3-Cl) | 3-chlorophenylalanine |
| Bta | 3-(3-benzothiophene) alanine |
| HoPhe, HomoPhe | High phenylalanine (α-amino acid) |
| Phe(4-tBu) | 4-tert-butylphenylalanine |
| HoSer, HomoSer | Homoserine (α-amino acid) |
| 2Pal, 2-Pal | 2-pyridylalanine, |
| 3Pal, 3-Pal | 3-pyridylalanine, |
| Phe(4-Cl) | 4-chlorophenylalanine |
| Tyr(Me) | O-methyl tyrosine, |
| Phe(4-Me) | 4-Methylphenylalanine |
| Cbz | carbobenzoxy- |
| Pro(di-F), Pro(diF), DifluoroPro, DiFluorPro | 4,4-difluoroproline |
| BetaAla, Beta-Ala | Beta-alanine |
| N-Me-Ala, NMe-Ala, NMeAla, N-MeAla | N-methyl alanine |
| N-Me-D-Ala, NMe-D-Ala, NMeD-Ala | N-methyl-D-alanine |
| N-Me-Leu, NMe-Leu, NMeLeu | N-methylleucine |
| N-Me-D-Leu, NMe-D-Leu, NMeD-Leu | N-methyl-D-leucine |
| Pro(4-NH$_2$), (4-aminoPro) | (2S,4R)-4-aminopyrrolidine-2-carboxylic acid |
| Thi | 3-(2-thienyl)-alanine |
| S-Pip | S-high proline, (S)-piperidine-2-formic acid |
| BetaHoLeu, BetaHomoLeu | Beta-homoleucine |
| HoLeu, HomoLeu | Homoleucine (α-amino acid) |
| D-HoLeu, D-HomoLeu | D-homoleucine (α-amino acid) |
| N-Me-HoLeu, N-Me-HomoLeu, NMe-HomoLeu | N-methyl homoleucine (α-amino acid) |
| N-Me-D-HoLeu, Me-D-HomoLeu, NMe-D-HomoLeu | D-N-methyl homoleucine (α-amino acid) |

TABLE 1-continued

Explanation of Amino Acid Abbreviations

| Abbreviation | Full name |
| --- | --- |
| Nle | N-leucine |
| Cha | 3-cyclohexylalanine |
| Sta | (3S,4S)-4-amino-3-hydroxy-6-methylheptanoic acid |
| stapled | Two olefin groups in the same peptide undergo olefin metathesis reaction to form a ring. |
| X | (S)-2-amino-2-methyl-6-heptenoic acid |
| BetaPhe | Beta-phenylalanine |
| BataHoPhe, BetaHomoPhe | Beta-homophenylalanine |
| Phe(2-Br) | 2-bromophenylalanine |
| Phe(pentaF) | Pentafluorophenylalanine |
| Phe(4-CF3) | (4-trifluoromethyl)-phenylalanine |
| Bpa | (4-benzoyl)-phenylalanine |
| Ala(dip) | 3,3-diphenyl alanine |
| NAsn | 2-((2-amino-2-oxoethyl)amino)acetic acid, |
| NLeu | N-(2-methylpropyl) glycine |
| NPhe | N-benzyl glycine |
| Phe(4-I) | 4-iodophenylalanine |
| 2Fua | 3-(2-furyl)-alanine |
| ACPA | 1-aminomethyl cyclopropylformic acid |
| PEG4 | 1-amino-3,6,9,12-tetraoxa-pentadec-15-acid, |
| PEG5 | 1-amino-3,6,9,12,15-pentaoxa-octadecyl-18-acid, |
| PEG8 | 1-amino-3,6,9,12,15,18,21,24-octaoxa-27C-27-acid, |
| PEG12 | 1-amino-3,6,9,12,15,18,21,24,27,30,33,36-dodecaoxa-39 carbon-39-acid, |
| ACPO | 3-Amino-1-Carboxymethyl-Pyridine-2-one |
| Aze | (S)-acridine-2-carboxylic acid |
| Bip | L-4,4'-biphenylalanine |
| Ac-Lys | |
| Palm, Palmitoyl | Palmitoyl |
| D-Phe(4-F) | D-4-fluorophenylalanine |
| A6c | 1-aminocyclohexyl formic acid |

TABLE 1-continued

Explanation of Amino Acid Abbreviations

| Abbreviation | Full name |
|---|---|
| azaPro | Pyrazole alkane-1-formic acid, (structure shown: pyrazolidine-1-carboxylic acid) |
| D-Phe(4-Cl) | D-4-chlorophenylalanine |
| D-Phe(3-Cl) | D-3-chlorophenylalanine |
| Tic | L-1,2,3,4-tetrahydroisoquinoline-3-carboxylic acid |
| Ind | L-indoline-2-carboxylic acid |
| R-Pip, (R)-Pip, HoPro, HomoPro | R-homoproline, (R)-piperidine-2-formic acid |
| S-Pip, (S)-Pip | S-homoproline, (S)-piperidine-2-formic acid |
| L-Pip | L-homoproline |
| Oic | L-octahydroindole-2-carboxylic acid |
| azaTic | 3,4-dihydrophthalazine-2(1H)-formic acid |
| N-Me-A6c, NMe-A6c, MeA6c | (1-methylamino)-cyclohexyl formic acid |
| D-Tic | D-1,2,3,4-tetrahydroisoquinoline-3-carboxylic acid |
| Phe(4-amidino), 4-(amidino)phenylalanine | 4-amidinophenylalanine |
| Phe(4-Pyrazol), Phe(4-Pyra), (S)-3-(4-(1H-pyrazol-1-yl)phenyl)-2-aminopropanoic acid | [4-(1H-pyrazol-1-yl)]phenylalanine |
| Aza-N-Me-Gly, azaNMeGly, aza-NMeGly | Aza-(N-methylglycine) |
| 1H-1,2,3-triazol-4-yl | Carboxyl-terminated —$CONH_2$ was substituted with 1H-1,2,3-triazol-4-yl |
| 2H-tetrazol-5-yl | Carboxyl-terminated —$CONH_2$ was substituted with 2H-tetrazole-5-yl |
| ψ(NHCO)51 | The —CONH— bond between amino acids 51 and 52 was replaced by —NHCO— bond. |
| ψ(NHCS)51 | The —CONH— bond between amino acids 51 and 52 was replaced by —NHCS— bond. |
| ψ(NH—CO—NH)51 | The —CONH— bond between amino acids 51 and 52 was replaced by —NH—CO—NH— bond. |
| Biotin | D-biotin, vitamin H |
| OEG | 2-(2-(2-aminoethoxy)ethoxy)acetic acid ($H_2N$-(CH$_2$CH$_2$O)$_2$-CH$_2$-COOH) |
| azaPhe | Azaphenylalanine, 1-benzylhydrazine-1-formic acid |
| cycloLeu | 1-aminocyclopentyl formic acid |
| BetaHoAla, BetaHomoAla | Beta-homoalanine |
| Cba | Beta-cyclobutylalanine, (structure shown) |
| Hexanoyl | Hexanoyl |
| Nonanoyl | Nonyl |
| Dodecanoyl | Dodecanoyl |
| C18 diacid | 1,18-octadecanedioic acid |
| Maleimide | Maleimide/Maleimide |
| Ahx | 6-aminocaproic acid |
| 3-[(1-methylpyridinium)-3-yl]alanine, (S)-3-(2-Amino-2-carboxyethyl)-1-methylpyridonium | (structure shown) |

TABLE 1-continued

Explanation of Amino Acid Abbreviations

| Abbreviation | Full name |
|---|---|
| Alg | (structure: allylglycine — H₂N-CH(CH₂CH=CH₂)-C(=O)-OH) |
| Deg | (structure: diethylglycine — H₂N-C(Et)(Et)-C(=O)-OH) |
| AlphaMeLeu | (structure: α-methyl leucine — H₂N-C(CH₃)(CH₂CH(CH₃)₂)-C(=O)-OH) |
| Cpa | (structure: cyclopropylalanine — cyclopropyl-CH₂-CH(NH₂)-C(=O)-OH) |
| ACBC | (structure: 1-amino-cyclobutane-carboxylic acid) |
| Cpg | (structure: cyclopropylglycine — cyclopropyl-CH(NH₂)-C(=O)-OH) |
| morpholino cyclic amino acid | (structure: 4-amino-tetrahydropyran-4-carboxylic acid) |
| beta-(thiazoly-4-yl)-L-Ala | (structure: β-(thiazol-4-yl)-L-alanine) |

The term "pharmaceutically acceptable salt" refers to a pharmaceutically acceptable organic or inorganic salt. Exemplary acid salts include, but are not limited to, sulfate, citrate, acetate, oxalate, chloride, bromide, iodide, nitrate, bisulfate, phosphate, acid phosphate, isonicotinic acid salt, lactate, salicylate, acid citrate, tartrate, oleate, tannate, pantothenate, hydrogen tartrate, ascorbate, succinate, maleate, fumarate, gluconate, glucuronic acid, gluconate, formate, benzoate, Glutamate, methanesulfonate, ethane sulfonate, benzenesulfonate, p-toluenesulfonate and pamoate (i.e., 1-1-methylene-bis (2-hydroxy-3-naphthalate)). The compound used in the present disclosure can form pharmaceutically acceptable salts with various amino acids. Suitable alkali salts include, but are not limited to, aluminum salts, calcium salts, lithium salts, magnesium salts, potassium salts, sodium salts, zinc salts, bismuth and diethanolamine salts.

See Handbook of Pharmaceutical Salts for a review of pharmaceutically acceptable salts: Properties, Selection, and Use (P. Heinrich Stahl and Camille G. Wermuth, ed., Wiley-VCH, 2002).

The term "crystal form" refers to one or more crystal structures formed by different arrangement of molecules in lattice space during crystallization.

The term "solvate" is a crystalline form that contains, in addition to active molecules, one or more solvent molecules incorporated into the crystalline structure. The solvate may include a stoichiometric amount or a non-stoichiometric amount of solvent, and solvent molecules in the solvent may exist in an ordered or non-ordered arrangement. Solvents containing non-stoichiometric amounts of solvent molecules can be obtained by the solvate losing at least some (but not all) of the solvent molecules. In a particular embodiment, a solvate is a hydrate, meaning that the crystalline form of the compound may include water molecules.

The term "prodrug" refers to a derivative of a compound containing a bioreactive functional group such that under biological conditions (in vitro or in vivo), the bioreactive functional group can be cleaved from the compound or otherwise react to provide the compound. In general, prodrugs are inactive, or at least less active than the compound itself, so that their activity cannot be exerted until the compound is cleaved from the bioreaction functional group. The bioreaction functional group can be hydrolyzed or oxidized under biological conditions to provide the compound. For example, the prodrug may contain a biohydrolyzable group, and examples of biohydrolyzable groups include, but are not limited to, biohydrolyzable phosphates, biohydrolyzable esters, biohydrolyzable amides, biohydrolyzable carbonates, biohydrolyzable carbamates, and biohydrolyzable ureides. For the summary of prodrugs, see, for example, J. Rautio et al., nature reviews drug discovery (2008) 7, 255-270 and prodrugs: Challenges and rewards (v. stella et al. ed., springer, 2007).

The term "alkyl" refers to a saturated linear or branched monovalent hydrocarbon group having one to eighteen carbon atoms (e.g., C1-C6 alkyl, also e.g., C1-C4 alkyl). Examples of alkyl include, but are not limited to, methyl, ethyl, 1-propyl, 2-propyl, 1-butyl, 2-methyl-1-butyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl.

The positive and progressive effect of the present disclosure is that the compound of the present disclosure has better stability and better activity to Kiss1R.

DETAILED DESCRIPTION OF THE PREFERRED EMBODIMENT

The following embodiments further illustrate the present disclosure, but the present disclosure is not limited thereto. The conditions of the experimental methods that didn't specified by the following embodiments were selected according to conventional methods and conditions, or according to the commercial instructions.

The peptide compounds of the present disclosure were all synthesized according to Lu et al (1981) *J. Org. Chem.* 46, 3433 and Fmoc-polyamide solid phase peptide synthesis method disclosed in its references. 9-fluorenylmethoxycarbonyl (Fmoc) group is used to provide a temporary protection for N-amino. Repeated removal of the highly alkali labile protecting group is performed using N,N-dimethylformamide containing 20% piperidine. The side chain functional groups can be protected by their butyl ethers (in the case of serine, threonine and tyrosine), butyl esters (in the case of glutamic acid and aspartic acid), butyl oxycarboxyl derivatives (in the case of lysine and histidine), trityl derivatives (in the case of asparagine and glutamine) and 4-methoxy-2,3,6-trimethylbenzenesulfonyl derivatives (in the case of arginine). When the C-terminal residue is glutamine or asparagine, a 4,4'-dimethoxybenzhydryl group is used to protect the side chain amino functional group. The solid phase carrier is based on a polydimethyl-acrylamide polymer composed of three monomers of dimethylacrylamide (main chain monomer), diallylethylenediamine (crosslinking agent) and acryloyl sarcosinate methyl ester (functionalizing reagent). The peptide-resin cleavable connecter used herein is the acid unstable 4-hydroxymethyl-phenoxyacetic acid derivative. Except for asparagine and glutamine, all amino acid derivatives were added as their prefabricated symmetric anhydride derivatives, while asparagine and glutamine were added using reverse N,N-dicyclohexylcarbodiimide/1-hydroxybenzotriazole mediated coupling method. All coupling and deprotection reactions were monitored using ninhydrin, trinitrobenzenesulfonic acid or isotin detection methods. When the synthesis was completed, the peptide was cleaved from the resin carrier, and at the same time, the protecting group of the side chain was removed by treatment with 95% trifluoroacetic acid containing 50% scavenger mixture. Scavengers that commonly used were ethanedithiol, phenol, anisole and water, and the accurate selection depended on the amino acid composition of the synthesized peptide. Trifluoroacetic acid was removed by vacuum evaporation, followed by grinding with diethyl ether to provide crude peptide. Any scavenger present was removed by a simple extraction step, wherein the crude peptide free of scavenger was provided by lyophilizing the aqueous phase. Reagents for peptide synthesis can be generally purchased from calbiochem-novabiochem (UK) ltd., Nottingham NG7 2QJ, uk. Purification can be achieved by any one or combination of techniques such as volume exclusion chromatography, ion exchange chromatography, and (mainly) reverse phase high performance liquid chromatography. Peptide analysis can be performed using thin layer chromatography, reversed-phase high performance liquid chromatography, amino acid analysis after acid hydrolysis, and rapid atom bombardment (FAB) mass spectrometry.

At the same time, the peptide compounds of the present disclosure can also be synthesized by liquid phase method well known to those skilled in the chemical and biochemical fields.

After synthesis, the peptide sequence of the active agent of the present disclosure can be purified using methods known in the art, such as HPLC and chromatography.

Embodiment 1

Preparation of Ac-Tyr-Asn-Trp-Asn-Ser-Phe-Gly-Leu-Arg-Phe-NH$_2$ (Compound YA-2)

Step 1: Polypeptides were synthesized by standard Fmoc chemistry. The basic operations were as follows. 5.0 g of commercially available Rink Amide MBHA resin (0.5 mmol/g) was swollen in DMF, and the resin was treated with 20 mL 20% piperidine/DMF for 20 minutes to remove Fmoc, repeated twice. The obtained resin was washed with DMF, 20 mL DMF solution of Fmoc-Phe-OH (2.9 g, 7.5 mmol), HATU (2.85 g, 7.5 mmol) and HOAt (1.04 g, 7.5 mmol) were added, then DIPEA (2.6 mL, 15 mmol) was added, the resin was treated at room temperature for 40 minutes, and the resin was washed with DMF to give Fmoc-Phe-Rink Amide MBHA resin. The resin was treated with 20 ml of 20% piperidine/DMF for 20 minutes to remove Fmoc, and the operation was repeated twice. The resin was washed with DMF, and a 20 mL DMF solution of Fmoc-Arg (PBF)-OH (5.0 g, 7.5 mmol), DIC (945 mg, 7.5 mmol) and HOBt (1.01 g, 7.5 mmol) was added to react overnight at room temperature. In a similar manner, amino acids such as Leu, Gly, Phe, SER (tBu), Asn (Trt), trp (Boc, Asn (Trt), D-Tyr (tBu) and the like were sequentially introduced to give $NH_2$-D-Tyr (tBu)-Asn (Trt)-Trp (Boc)-Asn (Trt)-Thr(tBu)-Phe-Gly-Leu-Arg-Phe-Rinkamide MBHA resin. The mixture was washed with DMF, added 10 mL DMF solution of AcOH (44 μL, 7.5 mmol), DIC (945 mg, 7.5 mmol) and HOBt (1.01 g, 7.5 mmol), reacted overnight at room temperature, then AC group was introduced. The resin was washed with DMF, DCM, methanol and methyl tert-butyl ether, and then drained to give 8.5 g of Ac-D-Tyr (tBu)-Asn(Trt)-Trp(Boc-Asn(Trt)-Thr(tBu)-Phe-Gly-Leu-Arg-Phe-Rinkamide MBHA resin.

Step 2: dried resin was added into 85 mL of TFA/TIS/EDT/H2O (94/2/2/2) solution, the mixture was stirred for 2 hours, filtered to remove the resin, and the resin was washed with 20 mL of TFA/TIS/EDT/$H_2O$ (94/2/2/2) solution. The filtrates were combined, cold diethyl ether (1000 mL) was added to the filtrate, and the resulting mixture was centrifuged at 3000 rpm for 3 minutes to remove the supernatant, and the solid was washed twice with diethyl ether and drained.

Step 3: The obtained crude polypeptide was dissolved with DMF, and then linear gradient elution (10 minutes) was performed with a flow rate of 25 mL/minute. Eluent AB was applied at a ratio of 74/26-64/36 using: eluent A: 0.05% TFA aqueous solution and eluent B: acetonitrile solution of 0.05% TFA, Sunfire C18, 10 μm, 120 column (19×250 mm) was applied on a preparative HPLC. The fractions containing the product were collected and lyophilized to give 1.1 g of white solid.

Embodiment 2

Preparation of Ac-(D-Tyr)-Hyp-Asn-Thr-Phe-azaGly-Leu-Arg (Me)-Trp-$NH_2$ (Compound YA-3)

Step 1: 5.0 g of commercially available Rink Amide MBHA resin (0.5 mmol/g) was swollen in DMF, and the resin was treated with 20 mL 20% piperidine/DMF for 20 minutes to remove Fmoc, repeated twice. The obtained resin was washed with DMF, 20 mL DMF solution of Fmoc-Trp (Boc)-OH (4.0 g, 7.5 mmol), HATU (2.85 g, 7.5 mmol) and HOAt (1.04 g, 7.5 mmol) was added, then DIPEA (2.6 mL, 15 mmol) was added, the resin was treated at room temperature for 40 minutes, and the resin was washed with DMF to give Fmoc-Trp(Boc)-Rink Amide MBHA resin. The resin was treated with 20 ml of 20% piperidine/DMF for 20 minutes to remove Fmoc, repeated twice. The resin was washed with DMF, and a solution of Fmoc-Arg (Me, Pbf)-OH (2.08 g, 3.0 mmol) in 20 mL DMF, DIC (945 mg, 7.5 mmol) and HOBt (1.01 g, 7.5 mmol) were added to react overnight at room temperature. The resin was treated with 20 mL 20% piperidine/DMF for 20 minutes to remove Fmoc, repeated twice. The resin was washed with DMF to give Arg (Me, Pbf)-Trp (Boc)-Rink amide MBHA resin. The obtained resin was added with 15 mL DMF solution of Fmoc-Phe-azaGly-Leu-OH (1.68 g, 3.0 mmol), DIC (945 mg, 7.5 mmol) and HOBt (1.01 g, 7.5 mmol), and reacted overnight at room temperature. The resin was treated with 20 mL 20% piperidine/DMF for 20 minutes to remove Fmoc, repeated twice. The resin was washed with DMF to give Phe-azaGly-Leu-Arg (Me, Pbf)-Trp (Boc)-Rink Amide MBHA resin. In a similar manner, amino acids such as Thr(tBu), Asn(Trt), Hyp(tBu), D-Tyr(tBu) and the like were sequentially introduced to give $NH_2$-D-Tyr(tBu)-Hyp(tBu)-Asn(Trt)-Thr(tBu)-Phe-azaGly-Leu-Arg(Me, Pbf)-Trp (Boc)-Rink Amide MBHA resin. The mixture was washed with DMF, then 10 mL DMF solution of AcOH (44 ml, 7.5 mmol), DIC (945 mg, 7.5 mmol) and HOBt (1.01 g, 7.5 mmol) were added, the reaction was performed overnight at room temperature to introduce Ac group. The resin was washed with DMF, DCM, methanol and methyl tert-butyl ether, and then drained to finally give 8.6 g of Ac-D-Tyr (tBu)-Hyp(tBu)-Asn(Trt)-Thr(tBu)-Phe-azaGly-Leu-Arg (Me, Pbf)-Trp(Boc)-Rink Amide MBHA resin.

Step 2: The dried resin was added into 85 mL of TFA/TIS/EDT/$H_2O$ (94/2/2/2) solution, the mixture was stirred for 2 hours, filtered to remove the resin, and the resin was washed with 20 mL of TFA/TIS/EDT/$H_2O$ (94/2/2/2) solution. The filtrates were pooled, cold diethyl ether (1000 mL) was added to the filtrate, and the resulting mixture was centrifuged at 3000 rpm for 3 minutes to remove the supernatant, and the solid was washed twice with diethyl ether and drained.

Step 3: The obtained crude precipitate was dissolved with DMF, and then linear gradient elution (17 minutes) was performed at a flow rate of 25 mL/minute. Eluent AB: 79/21-69/31 using: eluent A: 0.05% TFA aqueous solution, eluent B: 0.05% TFA acetonitrile solution was applied on a preparative HPLC using Phenomenex Gemini 10μ, 110 Å column (21.2×250 mm). The fractions containing the product were collected and lyophilized to give 1.2 g of trifluoroacetate, and 1.0 g of acetate was obtained by salt conversion, all of which were white solids.

Embodiment 3

Preparation of Ac-Phe(4-Cl)-Hyp-Asn-Thr-Phe-azaGly-Leu-Arg(Me)-Trp-$NH_2$ (Compound YA-72)

Similar to the synthesis method of Embodiment 2, while Fmoc-Phe(4-Cl)—OH(3 equivalents) was used instead of Fmoc-D-Tyr(tBu)-OH, HBTU/HOBt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-72 was isolated and purified by HPLC, and eluted with linear gradient (10 minutes) at a flow rate of 30 mL/minute, and eluent A/B: 61/39-54/46, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 12.4 mg of white solid.

Embodiment 4

Preparation of Ac-Tyr(Me)-Hyp-Asn-Thr-Phe-azaGly-Leu-Arg(Me)-Trp-$NH_2$ (Compound YA-73)

Similar to the synthesis method of Embodiment 2, while Fmoc-Tyr(Me)-OH (3 equivalents) was used instead of Fmoc-D-Tyr(tBu)-OH, HBTU/HOBt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-73 was isolated and purified by HPLC, and eluted with linear gradient (10 minutes) at a flow rate of 25 mL/minute, and eluent A/B: 76/24-68/32, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 4.7 mg of white solid.

Embodiment 5

Preparation of Ac-Phe(4-tBu)-Hyp-Asn-Thr-Phe-azaGly-Leu-Arg(Me)-Trp-NH$_2$ (Compound YA-75)

Similar to the synthesis method of Embodiment 2, while Fmoc-Phe(4-tBu)-OH (3 equivalents) was used instead of Fmoc-D-Tyr(tBu)-OH, HBTU/HOBt/DIPEA was used as condensation conditions, DMF was used as solvent, and the mixture was reacted at room temperature for 3 hours. The resin was washed and dried. The target polypeptide was cleaved from the resin and deprotected by the method of Step 2 of Embodiment 2. The crude product YA-75 was isolated and purified by HPLC, and eluted with linear gradient (10 minutes) at a flow rate of 30 mL/minute. Eluent A/B: 62/38-56/44, using: eluent A: 0.05% TFA aqueous solution, eluent B: 0.05% TFA acetonitrile solution, Sunfire C18, 10 μm, 120 column (19×250 mm) was applied on a preparative HPLC. The fractions containing the product were collected and lyophilized to give 5.9 mg of white solid.

Embodiment 6

Preparation of Ac-D-Tyr-A6c-Asn-Thr-Phe-azaGly-Leu-Arg(Me)-Trp-NH$_2$ (Compound YA-172)

Similar to the synthesis method of Embodiment 2, while Fmoc-A6c-OH (3 equivalents) was used instead of Fmoc-Hyp(tBu)-OH condensation, HATU/HOAt/DIPEA was used as condensation condition, DMF was used as solvent, and the mixture was reacted at room temperature for 3 hours. The resin was washed and dried. The target polypeptide was cleaved from the resin and deprotected by the method of Step 2 of Embodiment 2. The crude product YA-172 was isolated and purified by HPLC, and then eluted with linear concentration gradient (10 minutes) at a flow rate of 25 mL/minute. Eluent AB: 67/33-57/43 using: eluent A: 0.05% TFA aqueous solution, eluent B: 0.05% TFA acetonitrile solution, was applied on a HPLC using Shimada Zu C18 10 μm, 120 column (2×21.2×250 mm). Fractions containing the product were collected and lyophilized to give 12.2 mg of white solid.

Embodiment 7

Preparation of Ac-[D-Phe(2,4-DiCl)]-(S-Pip)-Asn-Thr-Phe-azaGly-Leu-Arg(Me)-Trp-NH$_2$ (Compound YA-182)

Similar to the synthesis method of Embodiment 2, while Fmoc-S-Pip-OH (3 equivalents) was used instead of Fmoc-Hyp(tBu)-OH condensation, HATU/HOAt/DIPEA was used as condensation condition, DMF was used as solvent, and the mixture was reacted at room temperature for 3 hours. Fmoc-[D-Phe (2,4-DiCl)]—OH (3 equivalents) was used to replace Fmoc-Tyr(tBu)-OH for condensation, HATU/HOAt/DIPEA was used as condensation condition, DMF was used as solvent, and the mixture was reacted for 3 hours at room temperature. The resin was washed and dried. The target polypeptide was cleaved from the resin and deprotected by the method of Step 2 of Embodiment 2. The crude product YA-182 was isolated and purified by HPLC. Linear gradient elution (10 minutes) was performed at a flow rate of 25 mL/minute, and eluent AB: 59/41-49/51, using: eluent A: 0.05% TFA aqueous solution, eluent B: 0.05% TFA acetonitrile solution, was applied on a HPLC using Phenomenex Gemini C18, 10 μm, 110 column (21.2×250 mm). The fractions containing the product were collected and lyophilized to give 20.2 mg of white solid.

Embodiment 8

Preparation of Ac-[D-Phe(2,4-DiCl)]-Hyp-Asn-Thr-Phe-azaPro-Leu-Arg(Me)-Trp-NH$_2$ (Compound YA-184)

Step 1: 0.4 g of commercially available Rink Amide MBHA resin (0.5 mmol/g) was swollen in DCM, and the resin was treated with 12 ml of 20% piperidine/DMF for 20 minutes to remove Fmoc, repeated twice. The obtained resin was washed with DMF, 10 mL DMF solution of Fmoc-Trp (Boc)-OH (320 mg, 0.6 mmol), HBTU (227 mg, 0.6 mmol) and HOBt (81 mg, 0.6 mmol) were added, then DIPEA (155 mg, 1.2 mmol) was added and treated at room temperature for 40 minutes. The resin was washed with DMF to give Fmoc-Trp(Boc)-Rink Amide MBHA resin. The resin was treated with 12 ml of 20% piperidine/DMF for 20 minutes to remove Fmoc, repeated twice. The resin was washed with DMF, 7 mL DMF solution of Fmoc-Arg (Me, Pbf)-OH (180 mg, 0.3 mmol), HATU (113 mg, 0.3 mmol) and HOAt (27 mg, 0.2 mmol) were added, then DIPEA (78 mg, 0.6 mmol) was added and treated at room temperature for 40 minutes. The resin was treated with 12 ml of 20% piperidine/DMF for 20 minutes to remove Fmoc, repeated twice. The resin was washed with DMF to give NH$_2$-Arg (Me, Pbf)-Trp (Boc)-Rink Amide MBHA resin. Fmoc-Phe-Azap-Leu (150 mg, 0.24 mmol), DIC (60 mg, 0.48 mmol) and HOBt (67 mg, 0.48 mmol) were added in 10 mL DMF solution. After overnight reaction at room temperature, HATU (182 mg, 0.48 mmol), HOAt (67 mg, 0.48 mmol) and DIPEA (62 mg, 0.48 mmol), and the reaction was continued at room temperature for 40 minutes. The resin was washed with DMF, and the resin was treated with 12 ml of 20% piperidine/DMF for 20 minutes to remove Fmoc, repeated twice. NH$_2$-Phe-Azap-Leu-Arg (Me, Pbf)-Trp (Boc)-Rink Amide resin was obtained. Thr(tBu), Asn(Trt), Hyp(tBu) and D-Phe(2,4-DiCl) were sequentially and gradually introduced in a Trp-like manner. The obtained resin was washed with DMF, Ac2O (184 mg, 1.8 mmol) and DIPEA (460 mg, 3.6 mmol) were added, the reaction was carried out at room temperature for 30 minutes, Ac groups were introduced, and the resin was washed by DMF, DCM, methanol and methyl tert-butyl ether and then drained to finally give Ac-[D-Phe (2,4-diCl)]-Hyp(tBu)-Asn(Trt)-Thr(tBu)-Phe-Azap-Leu-Arg(Me,Pbf) Trp(Boc)-Rink Amide MBHA resin.

Step 2: The dried resin was added to 10 mL of TFA/TIS/EDT/H$_2$O (94/2/2/2) solution, then the mixture was stirred for 2 hours, filtered to remove the resin, and the resin was washed with 2 mL of TFA/TIS/EDT/H$_2$O (94/2/2/2) solution. The filtrates were combined, ether (70 mL) was added to the filtrate, and the resulting mixture was centrifuged at 3000 rpm for 3 minutes to remove the supernatant, and the solid was washed twice with ether and drained. The obtained precipitate was dissolved in DMF and then eluted with a linear concentration gradient (10 minutes) at a flow rate of 25 mL/minute. Eluent AB: 66/34-58/42, using: eluent A: 0.05% TFA aqueous solution, eluent B: 0.05% TFA acetonitrile solution, was applied on a HPLC using Xtimate C18, 10 μm, 120 column (20×250 mm). The fractions containing the product were collected and lyophilized to give 5.9 mg of white solid.

Embodiment 9

Preparation of Ac-[D-Phe(2,4-DiCl)]-DiFluorPro-Asn-Thr-Phe-ψ(NHCS) Gly-Leu-Arg(Me)-Trp-NH$_2$ (Compound YA-255)

313 mg of commercially available Rink Amide MBHA resin (0.32 mmol/g) was swollen in DMF, and the resin was treated with 5 ml of 20% piperidine/DMF for 20 minutes to remove Fmoc, repeated twice. The obtained resin was washed with DMF, 5 mL DMF solution of Fmoc-Trp (Boc)-OH (158 mg, 0.3 mmol), HATU (114 mg, 0.3 mmol), HOAt (41 mg, 0.3 mmol) were added, and then DIPEA (77 mg, 0.6 mmol) was added. Treatment was carried out at room temperature for 40 minutes, and Trp (Boc) was introduced thereto to give Fmoc-Trp (Boc)-Rink Amide MBHA resin. The resin was treated with 5 ml of 20% piperidine/DMF for 20 minutes to remove Fmoc, repeated twice. The obtained resin was washed with DMF, 5 mL DMF solution of Fmoc-Arg (Me, Pbf)-OH (99 mg, 0.15 mmol), Hatu (57 mg, 0.15 mmol), HOAt (21 mg, 0.15 mmol) was added, and then DIPEA (39 mg, 0.3 mmol) was added. After treatment at room temperature for 1 hour, the resin was washed with DMF to give Fmoc-Arg (Me, Pbf)-Trp (Boc)-Rinkamide MBHA resin. Other amino acids Fmoc-Phe-ψ(NHCS)Gly-Leu-OH, Fmoc-Thr(OtBu)-OH, Fmoc-Asn(Trt)-OH, Fmoc-DiFluorPro-OH, Fmoc-[D-Phe(2,4-DiCl)]—OH were introduced in a similar manner to give Fmoc-[D-Phe(2,4-DiCl)]-DiFluorPro-Asn(Trt)-Thr(OtBu)-Phe-ψ(NHCS)Gly-Leu-Arg(Me)-Trp(Boc)-Rink Amide MBHA resin. The resin was treated with 5 ml of 20% piperidine/DMF for 20 minutes to remove Fmoc, repeated twice. The resin was washed with DMF, 5 mL DMF solution of glacial acetic acid (36 mg, 0.6 mmol), HBTU (227 mg, 0.6 mmol), HOBt (81 mg, 0.6 mmol) were added, then DIPEA (155 mg, 1.2 mmol) was added, the resin was treated at room temperature for 40 minutes, DMF, DCM, methanol and methyl tert-butyl ether were washed and then drained to give Ac-[D-Phe(2,4-DiCl)]-DiFluorPro-Asn(Trt)-Thr(OtBu)-Phe-ψ(NHCS)Gly-Leu-Arg(Me)-Trp(Boc)-Rink Amide MBHA resin.

The dried resin was added to 10 mL of TFA/TIS/H$_2$O (92/4/4) solution, the mixture was stirred for 2 hours, the resin was removed by filtration, and the resin was washed with 1 mL of TFA/TIS/H$_2$O (92/4/4) solution. The filtrates were combined, methyl tert-butyl ether (110 mL) was added to the filtrate, the resulting mixture was centrifuged at 3000 rpm for 1 minute, and the solid was washed twice with cold diethyl ether and drained. The obtained precipitate was dissolved in DMF and then eluted with a linear concentration gradient (10 minutes) at a flow rate of 25 mL/minute. Eluent AB: 64/36-54/46 Use: Elution A: 0.05% TFA aqueous solution, eluent B: 0.05% TFA acetonitrile solution was applied on a preparative HPLC using XTIMATE, 10 μm, 120 columns (20×250 mm). The fraction containing the product (the peak with the later retention time of the two peaks of the same molecular weight) was collected and lyophilized to give 3.8 mg of white solid.

TABLE 2

| Compound number (SEQ. ID NO.) | | Sequence | Mw (obs.) [M + 2H]$^{2+}$/2 | Mw (cal.) | Rt (min.) HPLC | HPLC purity analysis conditions | Preliminary measurement data (GPR54 EC50, nM) |
|---|---|---|---|---|---|---|---|
| YA-172 (1) | M10[Ac, D-Y45, A6c46, des47, T49, azaGly51, R(Me)53, W54] | Ac-(D-Tyr)-A6c-Asn-Thr-Phe-azaGly-Leu-Arg(Me)-Trp-NH$_2$ | 619.4 | 1237.41 | 15.10 | C | 0.012 |
| YA-182 (2) | M10[Ac, D-Phe(2,4-diCl)45, S-Pip46, des47, T49, azaGly51, R(Me)53, W54] | Ac-[D-Phe(2,4-DiCl)]-(S-Pip)-Asn-Thr-Phe-azaGly-Leu-Arg(Me)-Trp-NH$_2$ | 638.5 | 1276.27 | 19.21 | J | 0.021 |
| YA-255 (3) | M10[Ac, D-Phe(2,4-diCl)45, Pro(diF)46, des47, T49, Gψ(NHCS)51, R(Me)53, W54] | Ac-D-Phe(2,4-DiCl)-DiFluorPro-Asn-Thr-Phe-ψ(NHCS)G-Leu-Arg(Me)-Trp-NH$_2$ | 657.4 | 1313.32 | 17.74 | J | 0.028 |
| YA-72 (4) | M10[Ac, Phe(4-Cl)45, Hyp46, des47, T49, azaGlv51, R(Me)53, W54] | Ac-Phe(4-Cl)-Hyp-Asn-Thr-Phe-azaGly-Leu-Arg(Me)-Trp-NH$_2$ | 622.5 | 1243.80 | 15.84 | B | 5.55 |
| YA-73 (5) | M10[Ac, tyr(Me)45, Hyp46, des47, T49, azaGly51, R(Me)53, W54] | Ac-Tyr(Me)-Hyp-Asn-Thr-Phe-azaGly-Leu-Arg(Me)-Trp-NH$_2$ | 620.5 | 1239.38 | 14.14 | C | 1.32 |
| YA-75 (6) | M10[Ac, Phe(4-tBu)45, Hyp46, des47, T49, azaGly51, R(Me)53, W54] | Ac-Phe(4-tBu)-Hyp-Asn-Thr-Phe-azaGly-Leu-Arg(Me)-Trp-NH$_2$ | 633.5 | 1265.46 | 16.24 | C | 18.7 |

TABLE 2-continued

| Compound number (SEQ. ID NO.) | | Sequence | Mw (obs.) [M + 2H]$^{2+}$/2 | Mw (cal.) | Rt (min.) HPLC | HPLC purity analysis conditions | Preliminary measurement data (GPR54 EC50, nM) |
|---|---|---|---|---|---|---|---|
| YA-189 (7) | M10[Ac, D-2Fua45, Hyp46, des47, T49, Aze51, R(Me)53, W54] | Ac-D-2Fua-Hyp-Asn-Thr-Phe-Aze-Leu-Arg(Me)-Trp-NH$_2$ | 613.0 | 1224.37 | 14.00 | C | 1.696 |
| YA-190 (8) | M10[Ac, Phe(4-F)45, Hyp46, des47, T49, Azc51, R(Me)53, W54] | Ac-Phe(4-F)-Hyp-Asn-Thr-Phe-Aze-Leu-Arg(Me)-Trp-NH$_2$ | 627.0 | 1252.39 | 14.73 | C | 3.893 |
| YA-192 (9) | M10[Ac, D-Y45, azaPro46, des47, T49, Aze51, R(Me)53, W54] | Ac-(D-Tyr)-azaPro-Asn-Thr-Phe-Aze-Leu-Arg(Me)-Trp-NH$_2$ | 618.4 | 1235.39 | 14.21 | C | 5.035 |
| YA-193 (10) | M10[Ac, D-Y45, Pro(diF)46, des47, T49, Aze51, R(Me)53, W54] | Ac-(D-Tyr)-Pro(diF)-Asn-Thr-Phe-Aze-Leu-Arg(Me)-Trp-NH$_2$ | 636.0 | 1270.39 | 14.36 | C | 1.365 |
| YA-211 (11) | M10[Ac, D-Phe(4-F)45, S-Pip46, des47, T49, Aze51, R(Me)53, W54] | Ac-[D-Phe(4-F)]-(S-Pip)-Asn-Thr-Phe-Aze-Leu-Arg(Me)-Trp-NH$_2$ | 626.0 | 1250.42 | 15.92 | C | 1.13 |
| YA-240 (12) | M10[Ac, D-Phe(2,4-diCl)45, S-Pip46, des47, T49, azaGly51, R(Me)53, W54, NHtBu] | Ac-[D-Phe(2,4-DiCl)]-(S-Pip)-Asn-Thr-Phe-azaGly-Leu-Arg(Me)-Trp-NHtBu | 667.2 | 1332.38 | 15.32 | L | 173 |
| YA-244 (13) | M10[Ac, D-Phe(4-F)45, A6c46, des47, T49, A6c51, R(Me)53, W54] | Ac-[D-Phe(4-F)]-A6c-Asn-Thr-Phe-A6c-Leu-Arg(Me)-Trp-NH$_2$ | 654.2 | 1306.53 | 18.64 | F | 1.17 |

The HPLC purity analysis conditions in above Table 2 are as follows:

Condition A: Elution A/B=95/5-35/65
Mobile phase: A: Water (0.01% TFA), B: ACN (0.01% TFA)
Mobile phase ratio: 5% B within 0-3 min, linear gradient elution 5-65% B within 20 min
Velocity: 1.2 ml/min
Column: Eclipse XDB-C18, 4.6*150 mm, 5 μm
Box temperature: 40° C.

Condition B: Elution A/B=95/5-35/65
Mobile phase: A: Water (0.01% TFA), B: ACN (0.01% TFA)
Mobile phase ratio: 5% B within 0-3 min, linear gradient elution 5-65% B within 20 min
Velocity: 1.0 ml/min
Column: AGLIENT ZORBAX Eclipse XDB, C18, 4.6*150 mm, 5 m
Temperature: 40° C.

Condition C: Elution A/B=95/5-35/65
Mobile phase: A: Water (0.01% TFA), B: ACN (0.01% TFA)
Mobile phase ratio: 5% B within 0-3 min, linear gradient elution 5-65% B within 20 min
Velocity: 1.0 ml/min
Column: SunFire C18, 4.6*150 mm, 3.5 μm
Temperature: 40° C.

Condition D: Elution A/B=95/5-35/65
Mobile phase: A: Water (0.05% TFA), B: ACN (0.05% TFA)
Mobile phase ratio: 5% B within 0-3 min, linear gradient elution 5-65% B within 20 min
Velocity: 1.2 ml/min
Column: Eclipse XDB-C18, 4.6*150 mm, 5 μm Condition E: Elution A/B=85/15-25/75
Mobile phase: A: Water (0.01% TFA), B: ACN (0.01% TFA)
Mobile phase ratio: 15% B within 0-3 min, linear gradient elution 15-75% B within 20 min
Velocity: 1.0 ml/min
Column: SunFire C18, 4.6*150 mm, 3.5 μm
Temperature: 40° C.

Condition F: Elution A/B=95/5-35/65
Mobile phase: A: Water (0.05% TFA), B: ACN (0.05% TFA)
Mobile phase ratio: 5% B within 0-3 min, linear gradient elution 5-65% B within 20 min
Velocity: 1.2 ml/min
Column: SunFire C18, 4.6*150 mm, 3.5 μm Condition G: Elution A/B=80/20-20/80
Mobile phase: A: Water (0.01% TFA), B: ACN (0.01% TFA)
Mobile phase ratio: 20% B within 0-3 min, linear gradient elution 20-80% B within 20 min
Velocity: 1.0 ml/min
Column: SunFire C18, 4.6*150 mm, 3.5 μm
Temperature: 40° C.

Condition H: Elution A/B=50/50-0/100
Mobile phase: A: Water (0.05% TFA), B: ACN (0.05% TFA)
Mobile phase ratio: 50% B within 0-3 min, linear gradient elution 50-100% B within 20 min
Velocity: 1.0 mL/min Column: XBridge Peptide BEH C18, 4.6*150 mm, 3.5 μm
Column temperature: 40° C.
Condition I: Elution A/B=80/20-5/95
Mobile phase: A: Water (0.01% TFA), B: ACN (0.01% TFA)
Mobile phase ratio: 20% B within 0-2 min, linear gradient elution 20-95% B within 25 min
Velocity: 1.0 mL/min
Column: SunFire C18, 4.6*150 mm, 3.5 μm
Column temperature: 40° C.
Condition J: Elution A/B=95/5-35/65
Mobile phase: Water (0.05% TFA), B: ACN (0.05% TFA)
Mobile phase ratio: 5% B within 0-3 min, linear gradient elution 5-65% B within 20 min
Velocity: 1.0 mL/min
Column: XBridge Peptide BEH C18, 4.6*150 mm, 3.5 μm
Column temperature: 40° C.
Condition K: Elution A/B=50/50-0/100
Mobile phase: A: A: Water (0.01% TFA), B: ACN (0.01% TFA)
Mobile phase ratio: 50% B within 0-3 min, linear gradient elution 50-100% B within 20 min
Velocity: 1.0 ml/min
Column: SunFire C18, 4.6*150 mm, 3.5 μm
Column temperature: 40° C.
Condition L: Elution A/B=80/20-5/95
Mobile phase: A: Water (0.05% TFA), B: ACN (0.05% TFA)
Mobile phase ratio: 20% B within 0-2 min, linear gradient elution 20-95% B within 25 min
Velocity: 1.0 ml/min
Column: XBridge Peptide BEH, 4.6*150 mm, 3.5 μm
Column temperature: 40° C.
Condition M: Elution A/B=80/20-20/80
Mobile phase: A: Water (0.05% TFA), B: ACN (0.05% TFA)
Mobile phase ratio: 20% B within 0-1 min, linear gradient elution 20-80% B within 20 min
Velocity: 1.0 mL/min
Column: XBridge Peptide BEH C18, 4.6*150 mm, 3.5 μm
Column temperature: 40° C.
Condition N: Elution A/B=70/30-0/100
Mobile phase: A: Water (0.05% TFA), B: ACN (0.05% TFA)
Mobile phase ratio: 30% B within 0-3 min, linear gradient elution 30-100% B within 20 min
Velocity: 1.0 mL/min
Column temperature: 40° C.
Column: XBridge Peptide BEH C18, 4.6*150 mm, 3.5 μm
Condition O: Elution A/B=65/35-0/100
Mobile phase: A: Water (0.05% TFA), B: ACN (0.05% TFA)
Mobile phase ratio: 35% B within 0-1 min, linear gradient elution 35-100% B within 20 min
Velocity: 1.0 mL/min
Column temperature: 40° C.
Column: XBridge Peptide BEH C18, 4.6*150 mm, 3.5 μm
Condition P: Elution A/B=65/25-45/55
Mobile phase: A: Water (0.05% TFA), B: ACN (0.05% TFA)
Linear gradient elution 25-45% B within 30 min
Velocity: 1.0 mL/min
Column temperature: 40° C.
Column: XBridge Peptide BEH C18, 4.6*150 mm, 3.5 μm
Condition Q: Elution AB=82/18-52/48
Mobile phase: A: Water (0.05% TFA), B: ACN (0.05% TFA)
Linear gradient elution 25-45% B within 30 min
Velocity: 1.0 mL/min
Column temperature: 40° C.
Column: XBridge Peptide BEH C18, 4.6*150 mm, 3.5 μm Effect Embodiment 1 Determination of Kiss1 Receptor (GPR54) Binding Activity of Kiss1 Receptor (GPR54) Agonist The binding activity test of each compound from the above the embodiments with kiss1 receptor (GPR54) was performed by fluorescence energy resonance transfer (FRET) detection technology to detect $EC_{50}$ values of polypeptides and peptide analogs. The cells used in this experiment were NFAT-bla CHO-K1 cells (k1720, invitrogen, thermosher) that express human kiss1 receptor (GPR54). The specific operations were as follows:

Day 1: Seeding Cells in Plate

1. Microscope (CKX41, OLYMPUS), object lens×4 times, ocular lens×10 times. The cells were ensured in a good condition.

2. Digesting the cells, adding 3 ml of 0.05% pancreatin into a culture dish; cells were placed in a 37° C., 5% $CO_2$ incubator for 2 minutes (Thermo Fisher). After the cells became round under the microscope, 7 ml of culture medium was added. The formula of culture medium was as follows: DMEM90%, dialzedfbS10, NEAA0.1 mM, HEPES25 mM, Penicillin 100 U/ml, Streptomycin 100 μm/ml, pH7.3. After blowing and stirring, it was transferred to 15 mL centrifuge tube (430790, Corning). Centrifuge at 1000 rpm for 5 min (5810R, Eppendorf) and the supernatant was discard.

3. Adding 7 mL of culture medium (DMEM+0.1% BSA), it was pipetting into single cell suspension, after counting with Bio-RAD counter, the cell density was adjusted to 312,500 cell s/ml.

4. Cells were inoculated into 384 well plates at 32 μL per well, and the cell number was controlled at 10000 cells/well. 32 μl of culture medium was added into the blank control.

Day 2: Dosing and Data Analysis 1. 1000× Compound Plate Configuration

1) The compound to be tested was prepared into 50 mM working solution with DMSO.

2) 40 μl of the working solution of the compound to be tested was added into column 2 of row A-H of U-shaped 96-well plate (3797, comings), and 60 μl of DMSO was added into column 3-11. 20 μl of compound solution was sucked from the second column to the third column with a multichannel pipette blowing and stirring evenly; 20 μl of compound solution was absorbed from the third column with a multichannel pipette, then added into the fourth column, blowed and stirred to mix well; the compound was serially diluted 4-fold to a total of 10 concentrations. Column 1 and column 12 of 96-well plates were supplemented with 40 μl DMSO.

2. Intermediate Plate Configuration

1) AU-shaped 96-well plate was used, 199 μL of culture medium (DMEM+0.1% BSA) was added to each well, 1 μL of diluted compound (or DMSO) was sucked from 1000× compound plate and added into the 96-well plate at the corresponding position, blowed and stirred to mix well.

2) Homemade positive compounds and compounds to be tested were added. The cell culture plate was took out from the incubator and cells state was observed under microscope. Diluted compound in the intermediate plate or DMSO was added into the cell, 8 μl per well.

3) Cells were cultured in 37° C. and 5% $CO_2$ for 4 hours.

3. The Substrate was Added to Detect the Binding of the Drug to the Receptor 1) 1 μmol/L CCF-4AM solution and buffer solution B, C, D were equilibrated to room temperature. LiveBLAZER™-FRET B/G Loading Kit (K1095, thermo Fisher) containing CCF-4AM and solution B, solution C, solution D were also available from Invitrogen (K1157, thermo Fisher).

2) 6× loading solution was prepared: 6 μl of CCF-4AM dissolved solution A, 60 μl of solution b, 904 μl of solution c, and 30 μl of solution D were pipetted into EP tube, blowed and stirred to mix well.

3) 8 μl of the above-mentioned liquid was sucked with a multichannel pipette, added into a 96-well plate, and incubated for 2 hours at room temperature.

4) The PerkinElmer detector was used to detect the luminous signals of each hole. FI mode, λex=409 nm, λem1=460 nm, λem2=530 nm.

4. Data Processing Using Graphpad Prism 5 (GraphPad Software. Inc)

Effective rate %=(Signal-Min)/(Max-Min)×100%. Max: the maximum binding value of high concentration positive compound to kiss1 receptor. Min: Minimum value of no binding of 0.1% DMSO to receptor. Signal: the signal value at the corresponding concentration of the compound. The $EC_{50}$ of the corresponding compound was obtained by fitting the parameter curve with the concentration of the compound and the corresponding effective rate, as shown in Table 3.

TABLE 3

$EC_{50}$ of each polypeptide

| Polypeptide number | GPR54 $EC_{50}$/nM | Polypeptide number | GPR54 $EC_{50}$/nM | Polypeptide number | GPR54 $EC_{50}$/nM |
| --- | --- | --- | --- | --- | --- |
| YA-72 | 5.55 | YA-182 | 0.021 | YA-193 | 1.365 |
| YA-73 | 1.32 | YA-189 | 1.696 | YA-211 | 1.13 |
| YA-75 | 18.7 | YA-190 | 24.3 | YA-240 | 173 |
| YA-172 | 0.012 | YA-192 | 2.170 | YA-244 | 1.17 |

The $EC_{50}$ of parts of the compounds listed in Table 3 was superior to TAK448, showing strong activity, indicating that the compounds of the present disclosure can effectively bind kiss1 receptor (GPR54) at the level of in vitro biochemical experiments, so the compounds of the present disclosure has the potential to become effective therapeutic drugs for tumors.

Effect Embodiment 2 Experimental Data on Plasma Stability of Some Compounds

1. Preparation of 50 mM Phosphate Buffer:

The 5.750 g $Na_2HPO_4$, 1.141 g $NaH_2PO_4$. and 4.095 g NaCl (Shanghai Titan) weighed was dissolved in 1000 mL ultrapure water and the pH was adjusted to 7.4 to give 50 mM phosphate buffer containing 70 mM NaCl. The prepared phosphoric acid buffer solution was stored in the refrigerator at 4° C. and was valid for one week.

2. Preparation of Compound Stock Solution:

1). 5 mg/mL of test compound: 5 mg of compound was weighted and dissolved in 1 mL of DMSO.

2). 20 mM control: 2.728 mg of Fuka was dissolved in 0.5 mL of DMSO. 3.878 mg of benzalkonium bromide was dissolved in 0.5 mL of DMSO (Amresco).

3. Preparation of Experimental Plasma:

The frozen plasma (human: Shanghai wise chemistry; Rats and mice: Shanghai Sciple-Bikai; Dogs and monkeys: Suzhou Xishan Zhongke) were taken out of the −80° C. refrigerator, immediately placed in a 37° C. water bath, slightly shaken to melt it, then the thawed plasma was poured into a centrifuge tube, centrifuged at 3000 rpm for 8 min, and the supernatant was taken for experiments. The pH value of plasma was detected by a pH Meter & Sensor (METTLER TOLEDO). Only plasma with a pH value between 7.4 and 8 was used in the experiment. The plasma was placed on an ice bath for later use.

4. Preparation of Administration Solution:

1). 125 g/ml test compound solution: 5 μL of 5 mg/mL test compound (see step 2) was added into 195 μL DMSO; 500 μM control solution: 20 mM control stock solution (see step 2) was added to 195 μL DMSO.

2). 0.5% BSA phosphate buffer solution: 0.05 g BSA was added to 10 mL phosphate buffer solution (see step 1);

3). 5 g/ml of test compound administration solution: 40 μL of 125 μg/mL of test compound solution was added into 960 μL 0.5% BSA phosphate buffer solution, stirred and mixed evenly, and the administration solution was preheated in a 37° C. water bath for 5 minutes.

20 μM reference substance administration solution: 40 μL of 500 μM reference substance administration solution was added into 960 μL 0.5% BSA phosphate buffer solution, stirred and mixed evenly, and the administration solution was preheated in a 37° C. water bath for 5 minutes.

5. 10 μL of 5 μg/mL of the test compound and 20 μM of the control substance administration solution were respectively added to the wells set at different time points (0 minutes, 1 hour, 2 hours and 4 hours) on the 96-well plate, and the number of duplicate samples was 3.

6. 500 μL of ACN (IS) containing 5% FA was added to the well set at 0 minute hour, then 90 μL of plasma was added, after mixing, sealing film was pasted and placed at 4° C. (number of duplicate samples was 3).

7. 90 μL of plasma was added to the wells with set time points of 1 hour, 2 hours and 4 hours respectively, the number of duplicate samples was 3, and timing was started (the final concentration of the test compound was 500 ng/ml; The control was 2 μM).

8. Then, when the timer shows 1 hour, 2 hours and 4 hours, 500 μL of ACN (IS) solution containing 5% FA were added to the holes, respectively, at corresponding time points to terminate the reaction, and after mixing, sealing films were pasted and placed at 4° C.

9. All samples (0 minutes, 1 hour, 2 hours and 4 hours) at different time points on a 96-well plate were shaken for 10 minutes at 600 rpm/min on an oscillator (MTS 2/4, IKA), and then the samples were centrifuged for 15 minutes at 5594×g in a centrifuge (Multifuge×3R, thermo Fisher).

10. 150 μL of supernatant was taken from the centrifuged sample and sent to LC-MS/MS for analysis (conventional polypeptide LC-MS/MS analysis method). The calculated half-life of the corresponding compounds were shown in Table 4.

TABLE 4

Experimental Data on Plasma Stability of Compounds

| Polypeptide number | Rat plasma (T½ (h)) |
|---|---|
| YA-172 | 9.42 |
| YA-182 | 5.32 |

Although specific embodiments of the present disclosure have been described above, those skilled in the art should understand that these were merely embodiments and various changes or modifications can be made to these embodiments without departing from the principles and essence of the present disclosure. Therefore, the scope of protection of the present disclosure was defined by the appended claims.

What is claimed is:

1. A peptide compound 3, a pharmaceutically acceptable salt thereof, a tautomer thereof, or a solvate thereof, wherein the peptide compound 3 is selected from the group consisting of the compounds shown below:

```
Ac-(D-Tyr)-A6c-Asn-Thr-Phe-azaGly-Leu-Arg(Me)-
Trp-NH₂;

Ac-[D-Phe(2,4-DiCl)]-(S-Pip)-Asn-Thr-Phe-azaGly-
Leu-Arg(Me)-Trp-NH₂; and

Ac-D-Phe(2,4-DiCl)-DiFluorPro-Asn-Thr-Phe-
ψ(NHCS)G-Leu-Arg(Me)-Trp-NH₂.
```

2. A pharmaceutical composition comprising the compound 3, the pharmaceutically acceptable salts thereof, the tautomers thereof, or the solvates thereof of claim 1, and pharmaceutical excipients.

3. The peptide compound 3, the pharmaceutically acceptable salt thereof, the tautomer thereof, or the solvate thereof of claim 1, wherein the peptide compound 3 is:

Ac-[D-Phe(2,4-DiCl)]-(S-Pip)-Asn-Thr-Phe-azaGly-
Leu-Arg(Me)-Trp-NH₂.

4. The peptide compound 3, a pharmaceutically acceptable salt thereof, a tautomer thereof or a solvate thereof according to claim 1, wherein the peptide compound 3 is:

Ac-[D-Phe(2,4-DiCl)]—(S-Pip)-Asn-Thr-Phe-azaGly-Leu-Arg(Me)-Trp-NH₂;

wherein, D-Phe(2,4-DiCl) is 2,4-dichloro-D-phenylalanine, S-Pip is (S)-piperidine-2-formic acid;
the $EC_{50}$ of effectively bind kiss1 receptor (GPR54) of the compound is <0.028 nM.

5. The peptide compound 3, a pharmaceutically acceptable salt thereof, a tautomer thereof or a solvate thereof according to claim 1, wherein the peptide compound 3 is:

```
Ac-(D-Tyr)-A6c-Asn-Thr-Phe-azaGly-Leu-Arg(Me)-
Trp-NH₂;
``` wherein, A6c is 1-aminocyclohexyl fonnic acid;
the $EC_{50}$ of effectively bind kiss1 receptor (GPR54) of the compound <0.028 nM.

6. The peptide compound 3, a pharmaceutically acceptable salt thereof, a tautomer thereof or a solvate thereof according to claim 1,
wherein the peptide compound 3 is: Ac-D-Phe(2,4-DiCl)-DiFluorPro-Asn-Thr-Phe-ψ(NHCS)G-Leu-Arg(Me)-Trp-NH₂;
wherein, D-Phe(2,4-DiCl) is 2,4-dichloro-D-phenylalanine, DiFluorPro is 4,4-difluoroproline; ψ(NHCS) is The —CONH— bond between Phe and G was replaced by NHCS bond; and
wherein the $EC_{50}$ of effectively bind kiss1 receptor (GPR54) of the compound <0.03 nM.

7. The peptide compound 3, a pharmaceutically acceptable salt thereof, a tautomer thereof or a solvate thereof according to claim 1,
wherein the peptide compound 3 is: Ac-[D-Phe(2,4-DiCl)]—(S-Pip)-Asn-Thr-Phe-azaGly-Leu-Arg(Me)-Trp-NH₂;
wherein, D-Phe(2,4-DiCl) is 2,4-dichloro-D-phenylalanine, S-Pip is (S)-piperidine-2-formic acid;
wherein the $EC_{50}$ of effectively bind kiss1 receptor (GPR54) of the compound is <0.028 nM; and
wherein the T½ of rat plasma of the compound is >5 h.

8. The peptide compound 3, a pharmaceutically acceptable salt thereof, a tautomer thereof or a solvate thereof according to claim 1,
wherein the peptide compound 3 is: Ac-(D-Tyr)-A6c-Asn-Thr-Phe-azaGly-Leu-Arg(Me)-Trp-NH₂;
wherein A6c is 1-aminocyclohexyl fonnic acid;
wherein the $EC_{50}$ of effectively bind kiss1 receptor (GPR54) of the compound <0.021 nM; and
wherein the T½ of rat plasma of the compound is >5.32 h.

* * * * *